United States Patent [19]

Wagner et al.

[11] Patent Number: 5,386,832
[45] Date of Patent: Feb. 7, 1995

[54] LIVER FUNCTION BREATH TEST USING AROMATIC AMINO ACIDS

[75] Inventors: David A. Wagner, Acton, Mass.; Martin A. Baker, Mahwah, N.J.; Peter A. Burke, Belmont, Mass.; R. Amour Forse, Brookline, Mass.; John D. Palombo, Medfield, Mass.; Bruce R. Bistrian, Ipswich, Mass.

[73] Assignees: New England Deaconess Hospital, Boston; Metabolics Solutions, Inc., Acton, both of Mass.

[21] Appl. No.: 75,662

[22] Filed: Jun. 11, 1993

[51] Int. Cl.$^6$ ............................. A61B 5/08; A61B 6/00
[52] U.S. Cl. ..................................... 128/665; 128/719; 128/898
[58] Field of Search ................. 424/1.81; 514/567; 436/57, 900; 73/23.3; 128/654, 659, 718, 719, 730, 664, 665, 898

[56] References Cited

U.S. PATENT DOCUMENTS 4,830,010  5/1989  Marshall .................. 128/630
5,100,779  3/1992  Watkins ................... 435/25

OTHER PUBLICATIONS

Shanbhogue et al., "Whole Body Leucine, Phenylalanine, and Tyrosine Kinetics in End-Stage Liver Disease Before and After Hepatic Transplantation" *Metabolism* Nov. 1987, vol. 36, No. 11, pp. 1047–1053, as abstracted in Medline, AN88038269.
Baker et al., "The aminopyrine breath test does not correlate with histologic disease severity . . . ," *Hepatology*, (1987 May–Jun.), 7(3):464–7, as abstracted in Medline AN87192470.
Schoeller et al., "Comparison of different methods expressing results of the aminopyrine breath test . . . ," *Hepatology*, (1982 Jul.–Aug.), 2(4):455–62 as abstracted in Medline, AN 82237831.
Hehir et al., "Abnormal Phenylalanine Hydroxylation and Tyrosine Oxidation in a Patient With Acute Fulminant Liver Disease With Correction by Liver Transplantation" *Gastroenterology* 1985, vol. 89, No. 3, pp. 659–663.
Neale et al., "The metabolism of $^{14}C$-labelled essential amino acids given by intragastric or intravenous infusion to rats on normal and protein-free diets" *British Journal of Nutrition* 1974, vol. 32, pp. 11–25.
Ball et al., "Influence of dietary protein concentration on the oxidation of phenylalanine by the young pig" *British Journal of Nutrition* 1986, vol. 55, pp. 651–658.

*Primary Examiner*—Robert L. Stoll
*Assistant Examiner*—Lara E. Chapman
*Attorney, Agent, or Firm*—Lahive & Cockfield

[57] ABSTRACT

A test for determining hepatic function has been developed. This test uses oral administration of isotope labeled phenylalanine or tyrosine, particularly $^{13}C$-phenylalanine, in a rapid breath test. In the preferred mode, the breath sample is analyzed using a mass spectrometer and compared with a standard. The breath test provides a dynamic rather than static determination of hepatic function and can be used for both early and late stage liver problems.

9 Claims, No Drawings

LIVER FUNCTION BREATH TEST USING AROMATIC AMINO ACIDS

BACKGROUND OF THE INVENTION

The present invention concerns the use of carbon-labeled aromatic amino acids, particularly phenylalanine and tyrosine, in a breath test for determining liver function. The test is exceptionally well-suited as a screening test for a variety of liver disorders including chronic liver disease such as cirrhosis, necrosis and hepatic degeneration due to hepatitis and other illnesses. The test can also provide quantitative information on liver function to identify the degree and progression of hepatic dysfunction. This information may be useful for planning liver transplants and other treatments.

Current tests for identification and management of liver dysfunction, are, primarily, static blood tests. These tests include measurements of specific enzyme activities such as aminotransferases or gamma glutamyl-transferases, measurements of serum albumin, bile acids and bile pigments in plasma and urine, cholesterol testing, and coagulation tests such as prothrombin levels. These tests do not measure liver function but rather only show abnormal values which result from liver cell destruction. These tests are carried out primarily by blood testing in laboratories, although some stat instruments and methods for testing certain of these materials have been developed, or are in the process of development.

The problem with these static tests is that they do not provide a dynamic model of liver function but rather an indication of the prior liver cell destruction. Accordingly, in order to determine whether there are hepatic problems which could lead to the destruction of liver cells at a later time, a dynamic rather than static test is necessary.

Although a few specific quantitative tests for measuring hepatic function have been developed to supplement the static blood screening tests, these have not been overly successful. These dynamic tests are primarily breath tests measuring drug metabolism instead of degradation of natural metabolites. Examples of this first group of tests utilize labeled aminopyrine, phenacetin, or methacetin. Another group of breath tests, the substrate metabolism tests, use labeled galactose or caffeine. There are also plasma tests using caffeine and galactose. A further group of tests are plasma-based (as opposed to breath) liver substrate clearance tests using dyes such as indocyamine green and bromosulfophthalein.

The aminopyrine breath test has been found useful for measuring liver function in patients with alcoholic cirrhosis or chronic acute hepatitis. This test has clinical utility because of its capacity to reflect residual functional microsomal mass and viable hepatic tissue. See, e.g., A. Baker et al., Sem. in Liver Dis. 3:318–329 (1983). However, this test is useful mainly in identifying patients in most severe stages of liver disease. The reason is that the aminopyrine test is a measure of late function of cholestatic liver disease, not a sensor or indicator of early stages of disease. In addition, this test has potential safety concerns and significant cross reactivities which limit its usage.

Phenacetin and methacitin are also microsomal substrates which have been used in breath tests to evaluation hepatic function. Both phenacetin and methacetin undergo deethylation, resulting in acetaldehyde formation, which is oxidized by the Krebs cycle to $CO_2$. However, the phenacetin and methacetin breath tests are not sensitive enough to evaluate mild liver disease.

The caffeine and galactose elimination breath tests are also useful in determining liver function but have problems of their own. The caffeine test is a quantitative measurement of hepatic microsomal metabolism while the galactose elimination test measures hepatic cytosolic function. The galactose breath test is a better discriminator of chronic liver damage then it is of mild liver damage but it is subject to diet interferences. Similarly, the caffeine test is inaccurate in cases of those who smoke or who have had environmental exposure of hazardous chemicals. The false positive results from this test, coupled with the very low $CO_2$ values from healthy individuals, lead to too many inaccuracies. The plasma tests utilizing caffeine and galactose also share these same problems.

The dyes which are used in certain plasma tests have caused fatal reactions and accordingly have to be used under very controlled conditions. In addition, these are difficult tests to run and correlate with liver function.

A few papers have shown that plasma levels of labeled tyrosine or phenylalanine can be correlated, to some degree, with liver function. For example, Hehir et al., "Abnormal phenylalanine hydroxylation and tyrosine oxidation in a patient with acute fulminant liver disease with correction by liver transplantation," Gastroenterology 89: 659–65663 (1985), shows that in cases of chronic liver disease sufficiently acute so as to require transplantation, the use of isotope labeled phenylalanine and tyrosine could differentiate liver function values from those with properly functioning livers. Similarly, in Shanbhogue et al., "Whole body leucine, phenylalanine, and tyrosine kinetics in end-stage liver disease before and after hepatic transplantation", Metabolism 36( 11 ): 1047–1053 (1987), a test was made using three different labeled amino acids (phenylalanine, tyrosine and leucine) in order to detect hepatic dysfunction. Again, the primary tests used were plasma levels of each of these amino acids but some breath tests were also carried out. The breath tests yielded somewhat inconclusive results while the plasma test results were somewhat better. However, the study used patients with acute hepatic problems awaiting, and then undergoing, liver transplants. There is no indication that these tests could be used to measure liver function in non-acute patients.

Further, the Shanbhogue et al. paper used deuterated phenylalanine, $^{13}C$-leucine and $^{14}C$-tyrosine. The three labels were used to try to track the end-stage liver disease, not in any predictive function. The study was carried out using infusion rather than single intravenous or oral dose and the values determined were quantitative rather than being compared against a standard as in the present test. As such, there was no indication of what any breath values meant nor were they correlated in any way with clinical states. Specifically, the phenylalanine values showed no correlation for patients with liver disease or dysfunction. This is in direct contrast to the present test. The breath test in Shanbhogue et al. was not used as a predicitive test but merely as a means to obtain measurements of amino acid flux. Shanbhogue was directed to determining what changes occurred in plasma levels of these amino acids, not breath levels. As such, this work in no way affects the novelty or inventiveness of the present application.

Accordingly, an object of the invention is to provide a method of determining impairment of liver function at early stage of progression.

Another object of the invention is to provide a quick, inexpensive method of determining liver function.

A further object of the invention is to provide a screening test for liver function which can be used to detect both early and late liver disorders.

These and other objects and features of the invention will be apparent from the following description.

SUMMARY OF THE INVENTION

The present invention features a method of determining hepatic function in a patient using a breath test. This breath test is sufficiently sensitive to allow detection of not just chronic hepatic conditions where the liver is already irreparable damaged but it also is able to uncover these conditions at an early stage because of its dynamic nature.

The method of the invention commences with a step of administering, preferrably orally, a dose of an isotope labeled aromatic amino acid selected from the group consisting of phenylalanine, tyrosine and mixtures thereof to a patient. Use of oral administration ensures that the liver, rather than some other organ, gets the first chance to metabolize the labelled amino acid. The aromatic amino acid is oxidized in the patient, the expired breath from the patient is collected, and the amount of isotope in the expired breath is analyzed. The amount of expired isotope determined is compared with the standard and this comparison yields a measure of hepatic function. If the aromatic amino acid is administered orally, it preferably is in a pharmaceutically acceptable carrier such as water or a sugar solution. Alternatively, it may be administered intravenously.

The preferred labeled isotope is a carbon isotope which yields expired carbon dioxide. The preferred carbon isotopes are $^{13}C$ and $^{14}C$, with $^{13}C$ being more preferred because it is a stable rather than a radioactive isotope.

Although any aromatic amino acid having labeled carbon atoms could be used, phenylalanine and tyrosine having a isotope label at the 1-carbon are preferred. This is because the 1-carbon is excised and exhaled as carbon dioxide at an early step in the oxidative process. As such, this shortens the time until meaningful results are obtained from the test. If a $^{13}C$ isotope is used, the preferred method of measurement is with a mass spectrometer.

The method of the invention can be used to detect hepatic dysfunction and disease by comparing a standard in the form of the mean value of expired isotope in a normal population with value determined from the test subject. This test can be used in identifying the presence of liver dysfunction caused by chronic liver diseases, fulminant hepatic failure, metabolic liver diseases, and liver dysfunction seen in septic or injured patients. For a further and more detailed description of these states, see *Hepatology Textbook of Liver Disease*, Zakim and Bayer, (W. B. Saunders 1990)

The invention is further explained in the following detailed description.

DETAILED DESCRIPTION OF THE INVENTION

The present invention features a breath test for determining problems in hepatic function. This test is a dynamic rather than a static test and shows hepatic function rather than merely liver cell degradation. The test is relatively inexpensive to carry out and yields rapid results. While radioactive isotopes can be used in the test, it preferably is carried out with stable isotopes.

The test is based, in part, on the discovery that there is a correlation between liver function and the oxidative metabolism of phenylalanine and tyrosine. The critical step for detection purposes appears to be the reaction from p-hydroxyphenylpyruvic acid to homogentistic acid, whereby the terminal carbon dioxide group is cleaved off the carboxyl side chain. This reaction is catalyzed by the enzyme hydroxyphenylpyruvic acid oxidase which is a copper-containing hydroxylase. This oxidation step is very complex and involves hydroxylation of the phenyl ring, oxidation, decarboxylation, and migration of the side-chain. This reaction is carried out almost entirely in the liver and, therefore, makes a good predictor of liver function. By labeling the terminal carboxyl carbon of phenylalanine or tyrosine (the carboxyl group released during this reaction), the test provides a rapid determination of hepatic function.

The following example will more clearly explain the invention and its efficacy.

Example

This example compares the values obtained for the breath test of the invention for test subjects having known hepatic disorders with a control group. The example shows that this rapid test is predictive of liver problems.

All of the participants in the test are first required to fast overnight. This minimizes metabolic effects of meal absorption and the contribution of endogenous label appearing in the breath from natural levels of the endogenous isotope in the diet. While the preferred isotope for use in the test is $^{13}C$, other carbon isotopes (or even nitrogen isotopes) could be used. At least two baseline breath samples are collected and the mean isotope value in these samples is used as a background. This background is subtracted from the $^{13}C$ levels determined following isotopic administration in order to obtain the change in $^{13}C$ level.

All breath samples, both those collected prior to administration of the isotope and those after administration, are collected with a commercially available breath sampler such as a Quintron AlveoSampler. These samplers have a mouthpiece and a collection bag with a one-way valve there between. The breath samples are trapped in a syringe and the contents of the syringe are injected into a 10mm evacuation tube such as a Exetainer tube.

In the preferred mode of the invention, $^{13}C$-phenylalanine is used as the isotope tracer. One hundred mg doses of L-1-$^{13}C$-phenylalanine are dissolved in 50 ml of water and the dose is administered orally. The dose bottle is washed with another 50ml of water and the wash is administered to the patient to make sure that all the phenylalanine was released from the dose bottle. Although intravenous or intramuscular administration of the isotope tracer could be used, the oral dose acts sufficiently and is much easier to administer.

Breath samples are collected every ten minutes for one hour after dosage. The amount of labeled isotope is measured using an isotope ratio mass spectrometer such a Europa Scientific Gas Isotope Ratio Mass Spectrometer (Europa Scientific, Inc., Cincinnati, Ohio). The ratio of $^{13}C$-$CO_2$ to $^{12}C$-$CO_2$ (mass ratio 45:44) is measured and compared to a reference $CO_2$ tank. The reference $CO_2$ is calibrated to the international PDB standard and the amount of labeled $^{13}C$ is determined by the following formula $$\text{Atom \% } ^{13}C = (^{13}C/^{12}C + ^{13}C) \times 100 \qquad (1)$$

The instrument provides analytical precision to 0.0002 Atom % $^{13}C$.

The mean Atom % $^{13}C$ values are subtracted to determine the Atom % Excess $^{13}C$. The % Dose Oxid (or percent dose oxidized) is calculated from formulas 2 and 3.

$$\text{Total } ^{13}C \text{ Excreted} = \%^{13}C(\text{from AUC}) \times 5 \times (\text{time in min.}) \times \text{Body Surface Area (m}^2\text{)} \qquad (2)$$

$$\text{\% Dose Oxid} = \text{Total } ^{13}C \text{ Excreted/Dose (mmoles)} \times 100\% \qquad (3)$$

Two groups of subjects were used to test the efficacy of the present system. The first group contained 16 normal subjects while the second had 12 patients with various levels of liver disease. The mean age for the control group was 44±14 years while the test subjects had a mean age of 49.6±9.6 years.

This was not a significant difference. Similarly, the weight for the control group was 70±15 kg, while the weight for the subject group was 80±20 kg, again something that was not significant. The time to maximum peak isotope value in the expired breath was 23±10 minutes for the control group and 41±16 minutes for the test subjects, a non-significant difference. However, there were significant differences in terms of maximum percent dose oxidized in any 10 minute period and cumulative percent oxidized over the hour. Table 1 shows the values for the control group

TABLE 1

| Subject Number | Sex | Age | Wt (kg) | Time to Max. Peak (min.) | Max. % Dose Oxidized/ 10 min. | Cumulative 1 hr % Dose Oxidized |
| --- | --- | --- | --- | --- | --- | --- |
| 1 | F | 32 | 55 | 20 | 2.46 | 8.56 |
| 2 | F | 61 | 55 | 20 | 4.53 | 15.53 |
| 3 | M | 61 | 64 | 50 | 1.48 | 3.96 |
| 4 | M | 35 | 83 | 30 | 1.48 | 6.52 |
| 5 | M | 64 | 83 | 30 | 1.57 | 7.14 |
| 6 | F | 44 | 61 | 20 | 2.81 | 9.86 |
| 7 | F | 63 | 51 | 10 | 2.82 | 11.12 |
| 8 | F | 30 | 59 | 30 | 1.20 | 3.78 |
| 9 | M | 37 | 75 | 10 | 2.31 | 7.34 |
| 10 | M | 58 | 80 | 30 | 1.05 | 4.44 |
| 11 | M | 58 | 109 | 20 | 1.65 | 6.21 |
| 12 | M | 33 | 65 | 20 | 2.19 | 7.78 |
| 13 | M | 29 | 59 | 10 | 2.37 | 7.71 |
| 14 | M | 29 | 82 | 20 | 2.60 | 7.50 |
| 15 | M | 37 | 77 | 20 | 2.11 | 7.57 |
| 16 | M | 35 | 64 | 30 | 1.75 | 6.83 | and Table 2 shows the same values for the subject group

TABLE 2

| Subject Number | Sex | Age | Wt (kg) | Time to Max. Peak (min.) | Max. % Dose Oxidized/ 10 min. | Cumulative 1 hr % Dose Oxidized |
| --- | --- | --- | --- | --- | --- | --- |
| 17 | F | 61 | 47 | 20 | 0.43 | 2.16 |
| 18 | M | 53 | 75 | 10 | 0.62 | 2.81 |
| 19 | M | 45 | 80 | 60 | 0.36 | 1.25 |
| 20 | F | 40 | 98 | 50 | 0.93 | 2.00 |
| 21 | F | 58 | 82 | 50 | 0.49 | 1.59 |
| 22 | M | 60 | 95 | 40 | 0.17 | 0.51 |
| 23 | M | 44 | 84 | 50 | 0.36 | 1.29 |
| 24 | F | 56 | 59 | 60 | 0.38 | 1.46 |
| 25 | M | 48 | 82 | 40 | 0.17 | 0.61 |
| 26 | M | 30 | 125 | 50 | 0.58 | 2.22 |
| 27 | M | 42 | 73 | 40 | 1.09 | 3.88 |
| 28 | F | 58 | 60 | 20 | 0.46 | 2.02 |

The maximum percent dose oxidized within 10 minutes for the control group was 2.15±0.84% while for the subject patients, it was 0.50±0.27%. This is significant with a student T test value of P<0.05. The results of the cumulative percent dose oxidized provide similar results. The cumulative percent dose oxidize for the controls had value of 7.62±2.87% while the test patients had values of 1.82±0.93%. Again, this is statistically significant with a P<0.05.

A review of the individual values on Tables 1 and 2 show the efficacy of this test even more clearly. With the exception of test patient 27, none of the values for the test patients overlap with the values of the control group. However, the fact that the values for patient 27 overlap with those for the control group is not surprising when one looks at the standard liver function tests for all of the test subjects. Table 3 lists the patient number, sex, age, weight, AST (aspartate aminotransferase) level, the ALT (alanine aminotransferase) level, the T BILI (total bilirubin) level, the PT (prothrombin time) level, the A Phos (alkaline phosphatase) level, and the ALB (albumin) level. In addition, the diagnosis of each of the patients is shown.

TABLE 3

| Subject Number | Sex | Age | Wt (kg) | AST | ALT | T BILI | PT | A PHOS | ALB | Diagnosis |
| --- | --- | --- | --- | --- | --- | --- | --- | --- | --- | --- |
| 17 | F | 61 | 47 | 111 | 57 | 8.8 | 13.0 | 285 | 3.1 | Primary Biliary Cirrhosis |
| 18 | M | 53 | 75 | 30 | 93 | 1.1 | 16.0 | 115 | 3.0 | Alcoholic Cirrhosis |
| 19 | M | 45 | 80 | 26 | 25 | 1.0 | 13.0 | 136 | 4.3 | Alcoholic Cirrhosis |
| 20 | F | 40 | 98 | 106 | 162 | 2.0 | 11.8 | 721 | 3.8 | Primary Sclerosing Cholangitis |
| 21 | F | 58 | 82 | 15 | 96 | 6.0 | 16.0 | 231 | 2.2 | Cirrhosis |
| 22 | M | 60 | 95 | 58 | 34 | 2.4 | 13.7 | 116 | 3.7 | Variceal Bleeding |
| 23 | M | 44 | 84 | 115 | 52 | 1.7 | 14.1 | 133 | 2.9 | Cirrhosis-Non A; Non B |
| 24 | F | 56 | 59 | 71 | 19 | 2.7 | 15.8 | 109 | 2.7 | Cirrhosis-Hepatitis C |
| 25 | M | 48 | 82 | 101 | 31 | 3.8 | 15.6 | 148 | 2.4 | Alcoholic Cirrhosis |
| 26 | M | 30 | 125 | 121 | 151 | 30 | 19.4 | 190 | 2.3 | Acute Hepatic Necrosis |
| 27 | M | 42 | 73 | 39 | 23 | 1.4 | 12.3 | 107 | 4.4 | Alcoholic Cirrhosis |
| 28 | F | 58 | 60 | 78 | 36 | 14 | 17.9 | 197 | 2.3 | Cirrhosis; Auto immune CAH |

The normal values for AST range from 10–35, normal ALT is 0–35, normal T BILI is 0.2–1.2, normal PT is 11–13, normal A Phos is 16–106 and normal ALB is greater than 3.2. As can be seen from Table 3, only patient 27, out of all the 12 patients, has static blood levels at, or near, normal. Accordingly, it is not surprising that his values on the breath test are closest to those of the control group.

In light of the foregoing, it is clear that the breath test of the invention can be used to show problems in liver function. This example is merely illustrative and not meant to be limiting in any way. Those skilled in the art will determine other modifications to the procedures described herein which are within the scope of the present invention. The present invention is defined by the following claims.

What is claimed is:

1. A method of determining hepatic functional activity in a subject comprising the steps of:

orally administering an effective amount of $^{13}$Carbon labeled phenylalanine to said subject;

allowing said $^{13}$Carbon labeled phenylalanine to be oxidized in said subject;

collecting expired breath from said subject;

measuring the amount of said $^{13}$Carbon in said expired breath; and comparing said amount of expired $^{13}$Carbon with a standard;

whereby said comparison yields a measure of hepatic functional activity.

2. The method of claim 1 wherein said phenylalanine is administered in a pharmaceutically acceptable carrier.

3. The method of claim 1 wherein said expired $^{13}$Carbon is in the form of carbon dioxide.

4. The method of claim 1 wherein said phenylalanine is labeled at the 1-carbon position.

5. The method of claim 1 wherein said phenylalanine comprises a plurality of said $^{13}$Carbons.

6. The method of claim 1 wherein said step of measuring comprises the step of making mass spectrometer measurements of said expired $^{13}$Carbon.

7. The method of claim 1 wherein said comparison is used to detect the presence of hepatic disease or dysfunction.

8. The method of claim 7 wherein said hepatic disease or dysfunction is a selected from the group consisting of chronic liver diseases, fulminant hepatic failure, metabolic liver diseases, and liver disfunction seen in septic or injured patients.

9. The method of claim 1 wherein said standard comprises the mean value of expired $^{13}$Carbon in a normal population.

* * * * *